United States Patent [19]

Karasawa

[11] Patent Number: 4,744,361
[45] Date of Patent: May 17, 1988

[54] RESECTOSCOPE

[75] Inventor: Hitoshi Karasawa, Hachioji, Japan

[73] Assignee: Olympus Optical Co., Ltd., Tokyo, Japan

[21] Appl. No.: 47,381

[22] Filed: May 8, 1987

[30] Foreign Application Priority Data

May 15, 1986 [JP] Japan .................. 61-073388[U]

[51] Int. Cl.⁴ .......................................... A61B 17/36
[52] U.S. Cl. ................................. 128/303.15; 128/4
[58] Field of Search ............ 128/4, 6, 303.13, 303.14, 128/303.15

[56] References Cited

U.S. PATENT DOCUMENTS

| | | | |
|---|---|---|---|
| 2,068,721 | 1/1937 | Wappler et al. | 128/303.15 |
| 3,939,839 | 2/1976 | Curtiss | 128/303.15 |
| 4,149,538 | 4/1979 | Mrava et al. | 128/303.15 |
| 4,423,727 | 1/1984 | Widran et al. | 128/303.15 |
| 4,430,996 | 2/1984 | Bonnet | 128/303.15 |
| 4,538,610 | 9/1985 | Kubota | 128/303.15 |
| 4,644,950 | 2/1987 | Valli | 128/303.15 |

FOREIGN PATENT DOCUMENTS 60-144406 9/1985 Japan .
61-33929 10/1986 Japan .

Primary Examiner—William H. Grieb
Attorney, Agent, or Firm—Armstrong, Nikaido, Marmelstein & Kubovcik

[57] ABSTRACT

A resectoscope comprising a hollow sheath, an observing scope inserted in the sheath, a resecting electrode inserted through the sheath and a handle part having a slider connected to the sheath, having the electrode connected at the base end to it and moving this electrode forward and rearward in the axial direction, wherein is provided an electrode fixing mechanism having an inserting hole which is provided in the slider and in which the electrode is inserted at the base end, an engaging part provided in the base end part of the electrode inserted in the inserting hole, an electrode fixing means having a locking part engaged with the engaging part provided in the electrode to lock the electrode and movable in the direction intersecting with the axis of the electrode, an energizing device energizing the electrode fixing member in the direction of fixing the electrode, an electrode fixing mechanism fixing device fixing the electrode fixing member and energizing device to the slider and a position adjusting device making the position of the electrode fixing member with respect to the slider adjustable in the direction intersecting with the axis of the electrode.

12 Claims, 5 Drawing Sheets

RESECTOSCOPE

BACKGROUND OF THE INVENTION:

1. Field of the Invention:

This invention relates to a resectoscope provided with a fixed position adjusting means in an electrode fixing mechanism for fixing an electrode.

2. Related Art Statement:

Recently, there has come to be extensively used an endoscope whereby an elongate insertable part can be inserted into a body cavity to observe the interior of the body cavity without incising it or to cure it by using a treatment tool.

For the above mentioned endoscope, there is a resectoscope which can be inserted through a urethra to resect a swollen prostate or the like.

In such resectoscope, an optical sighting tube for observation and an electrode as a resecting means are inserted through a hollow sheath and this electrode is fixed at the rear end to an electrode fixing mechanism provided in a slider of a handle so as to project out of and retreat into the front end of the sheath.

In such electrode fixing mechanism shown in U.S. Pat. No. 4,149,538, the electrode is fixed by the engagement of an offset provided at the rear end of the electrode with an opening provided in a plunger reciprocatable in the direction intersecting with the axial direction of the electrode.

Also, in the one shown in the Gazette of Japanese Utility Model Publication No. 33,929/1986, an electrode fixing member is provided within a movable member fixing the electrode at the rear end and is provided with a slit to form a flexing piece, an electrode holding space is formed within this slit and a pressing part pressing the flexing piece on the side to narrow the width of the above mentioned slit or the electrode holding space is provided on the side of the above mentioned movable member.

In these related art examples, an operation of pushing a button or rotating a grip was necessary to fix the electrode.

On the other hand, in the Gazette of Japanese Utility Model Laid Open No. 144,406/1985, there is shown an electrode fixing mechanism whereby the electrode is automatically fixed by the operation of inserting the electrode into an electrode inserting hole.

This related art example shall be explained with reference to FIGS. 6 and 7.

That is to say, an inserting hole 3 with which an electrode 2 is to be engaged on the rear end side is provided on the front end surface side of a slider 1. On the other hand, there is formed an incised recess 5 which communicates with the depths of the hole 3 from the side intersecting at right angles with this inserting hole 3 and in which a guide frame 4 made of a metal to lock the above mentioned electrode 2 at the rear end is to be contained. The guide frame 4 contained in this recess 5 is provided with a hole 6 in the position facing the above mentioned inserting hole 3 so that the electrode 2 may pass at the rear end through this hole 6 and may collide at the rear end with the recess opposed to this hole 6. An electrode fixing member 8 provided with an electrode fixing incision 7 is engaged on the tip side with this guide frame 4. A sloped part 9 projecting on the inserting depth side of the electrode 2 is formed in this incision 7. On the other hand, the electrode 2 is provided near the rear end with an incision 11 so as to be fixed as prevented by this sloped part from being removed. Outside the above mentioned electrode fixing member 8, a guide frame fixing member 12 pressing and fixing the above mentioned guide frame 4 in a predetermined position is pressed into the recess of the slider 1. This guide frame fixing member 12 is cylindrical, has the electrode fixing member 8 slidably inside it and is covered on the outer periphery with a cap 14 through a coil spring 13. The electrode fixing member 8 is energized by the above mentioned coil spring 13 in the direction of projecting out of the recess of the slider 1 together with the cap 14. The sloped part 9 is set by this energiging force to project in the center direction of the hole 6 from the peripheral edge position of the hole 6 of the guide frame 4 communicating with the inserting hole 3. Therefore, in case the electrode 2 inserted through this hole 6 is inserted at the rear end to the depth side by pressing this sloped part 9 (energized by the coil spring 13) and in case the electrode 2 is inserted in the incision 11 near the rear end over the sloped part 9, the sloped part 9 pressed and moved by the energizing force of the coil spring 13 will be returned and will remain engaged with the incision 11 and the electrode 2 will be automatically fixed. By the way, on the outer periphery near the end of the guide frame fixing member 12, a recess is formed in the part opposed to the inner periphery of the cap 14 and is fitted with a watertight O-ring 15. In FIG. 6, the reference numeral 16 represents a scope guide tube and 17 represents an electrode cord connector.

In the structure of the above mentioned related art example, as no mechanism of adjusting the position of the sloped part 9 of the electrode fixing member 8 is provided, there has been a defect that, due to the fluctuation of the dimensions of the parts forming the electrode fixing mechanism and the faulty adjustment in assembling, in case the electrode 2 is inserted, it will not collide at the rear end with the sloped part 9 and will not be sufficiently fixed.

OBJECTS AND SUMMARY OF THE INVENTION

An object of the present invention is to provide a resectoscope wherein the position of the electrode fixing member can be easily adjusted.

Another object of the present invention is to provide a resectoscope wherein the electrode can be positively fixed.

Further, another object of the present invention is to provide a resectoscope wherein, even if the dimensions of the parts forming the electrode fixing mechanism fluctuate, the parts can be simply set in the positions adapted to fixing.

The present invention relates to a resectoscope comprising a hollow sheath, an observing scope inserted in the above mentioned sheath, a resecting electrode means inserted through the above mentioned sheath, a handle part having a slider connected to the above mentioned sheath, having the above mentioned electrode means connected at the base end to it and moving this electrode means forward and rearward in the axial direction and an electrode fixing mechanism having an inserting hole which is provided in the above mentioned slider and in which the above mentioned electrode is inserted at the base end, an engaging part provided in the base end part of the electrode means inserted in this inserting hole, an electrode fixing member having a locking part engaged with the engaging part provided in the above mentioned electrode means to lock this electrode means and movable in the direction intersecting with the axis of the above mentioned electrode, an energizing means energizing the above mentioned electrode fixing member in the direction of fixing the above mentioned electrode, an electrode fixing mechanism fixing means fixing the above mentioned electrode fixing member and energizing means to the above mentioned slider and a position adjusting means making the position of the electrode fixing member with respect to the above mentioned slider adjustable in the direction intersecting with the axis of the above mentioned electrode.

The other features and advantages of the present invention will become apparent enough with the following explanation.

BRIEF DESCRIPTION OF THE DRAWINGS

FIG. 1 is a magnified sectioned view on line A—A in FIG. 3, showing an electrode fixing mechanism part.

FIG. 2 is a side view showing a resectoscope.

FIG. 3 is a magnified sectioned view showing a partial peripheral side on which the electrode fixing mechanism in FIG. 2 is formed.

FIG. 4 is a sectioned view showing an electrode fixing mechanism part.

FIG. 5 is a sectioned view showing the position adjusting member in FIG. 4 as rotated to be moved to the upper side.

FIG. 6 is a sectioned view showing an electrode fixing mechanism part.

FIG. 7 is a sectioned view in the direction intersecting at right angles with FIG. 6.

DETAILED DESCRIPTION OF THE PREFERRED EMBODIMENTS

Figure 1:
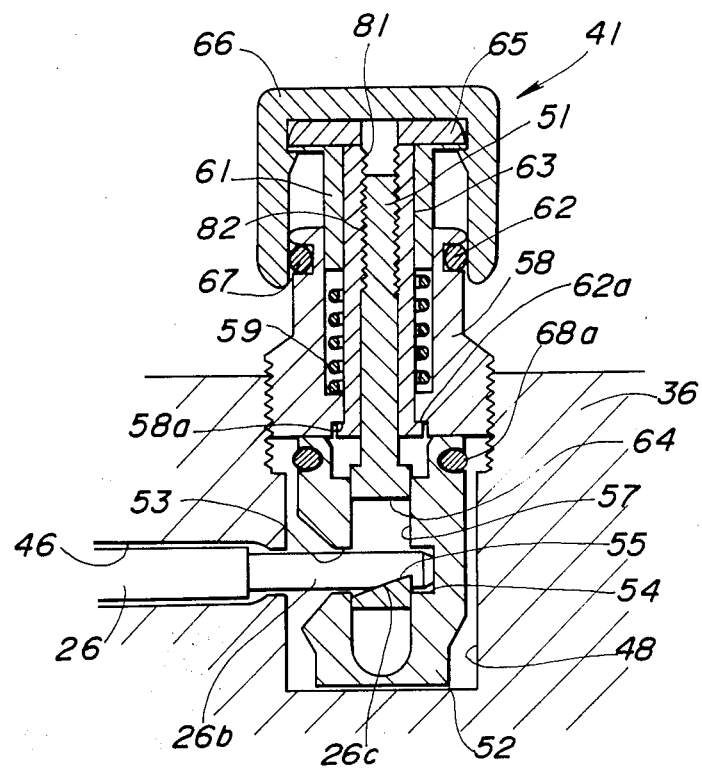
FIGS. 1 to 3 relate to the first embodiment of the present invention.
Figure 2:
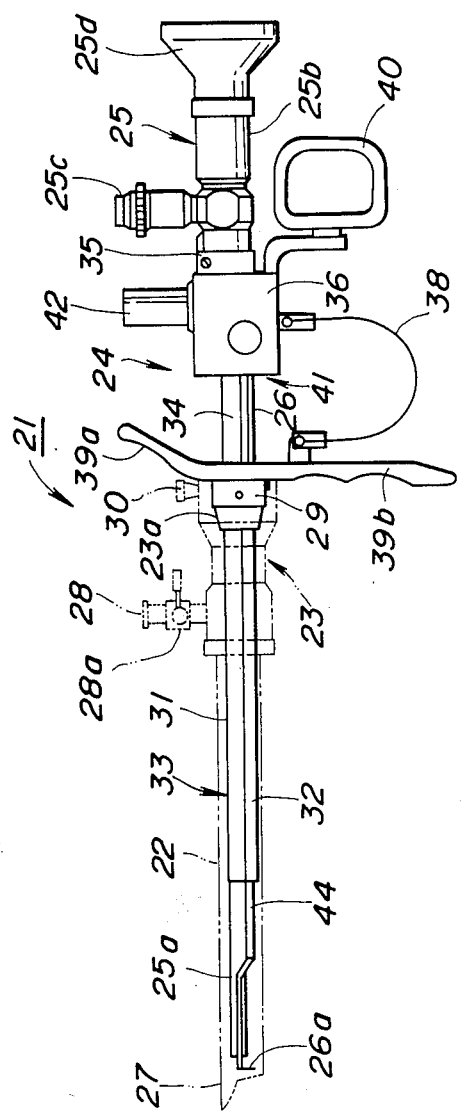
Figure 3:
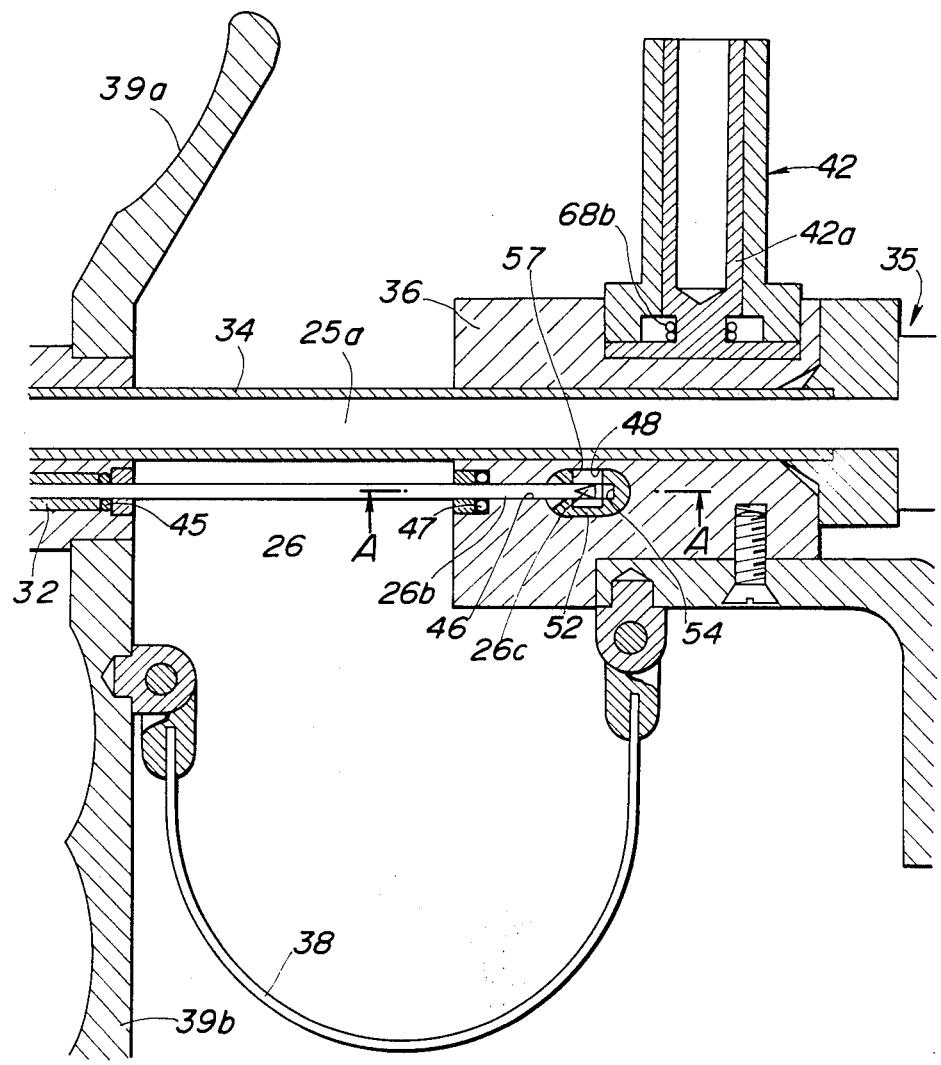

FIGS. 1 to 3 show the first embodiment of the present invention.

A resectoscope 21 provided with the first embodiment as shown in FIG. 2 is formed of a combination of a sheath body 23 provided with a hollow sheath 22 shown by the two-point chain lines to project forward, a (resecting) handle 24 connected to this sheath body 23, an optical sighting tube (scope) 25 inserted through the sheath 22 from the rear of the handle 24 and an electrode rod 26 inserted through the sheath 22 from the above mentioned handle 24. The above mentioned sheath 22 is formed to be elongate so as to be able to be inserted into a urethra and has an insulated beak 27 connected to the tip. This sheath 22 may be formed of an insulating material integrally with the insulated beak 27. The above mentioned sheath body 23 has a water feeding port 28 provided with a cock 28a and feeding an irrigating liquid into a bladder through the sheath 22, has a fitting inlet 23a into which a connecting part 29 of the handle 24 can be fitted to be secured and is provided with a removable button 30 engaging and disengaging, for example, a clicking mechanism for fixing this handle connecting part 29 within the fitting inlet 23a. A handle inserting part 33 consisting of a scope guide tube 31 through which the inserted part 25a of the scope 25 is inserted and an electrode guide tube 32 through which the electrode rod 26 is inserted is connected in front of the connecting part 29 of the above mentioned handle 24 and is inserted into the sheath 22. Also, the connecting part 29 of this handle 24 is provided with a guide shaft 34 to project rearward in the axial direction. A scope connecting part 35 is formed at the rear end of this guide shaft 34. On the other hand, a slider 36 sliding in the axial direction along the guide shaft 34 is arranged between the above mentioned front connecting part 29 and rear scope connecting part 35. This slider 36 is energized to contact, for example, with the rear scope connecting part 35 by a spring 38 set between the slider 36 and the front connecting part 29. By the way, the above mentioned spring 38 is a plate spring in the illustrated example but may be a coil spring. The above mentioned handle connecting part 29 is provided with finger rests 39a and 39b to project respectively above and below. The slider 36 also has a finger resting O-ring 40 downward in the rear.

The above mentioned slider 36 has an electrode fixing mechanism part 41 of the first embodiment wherein the electrode rod 26 is inserted from the front and is removably fixed. A connector 42 for passing a high frequency current through this connected electrode rod 26 from a high frequency cauterizing current source not illustrated is provided to project on the slider 36. The electrode rod 26 fixed to this slider 36 and provided to project forward is projected forward through the electrode guide tube 32 provided to project forward from the inserting hole formed in the connecting part 29 of the handle 24 and from this connecting part 29.

The scope connecting part 35 of the handle 24 is so made as to removably insert and connect the scope 25. The connected scope 25 is inserted through the above mentioned scope guide tube 31 provided as extended to the rear scope connecting part 35 from the front connecting part 29 so as to project forward of the guide tube 31 on the tip side of an insertable part 25a. By the way, in the illustrated example, the rearward extended part of the scope guide tube 31 is also the guide shaft 34 but this guide shaft may be separately provided. The above mentioned scope 25 is formed of a body 25b, a forward connected elongate insertable part 25a, a light guide connector 25c and an eyepiece 25d. A light guide fiber leading an illuminating light to the insertable part 25a tip and an image transmitting optical system transmitting an observed image from the tip of the insertable part 25a to the eyepiece 25d are arranged within this scope 25.

A resecting tip electrode 26a in the form, for example, of a loop is formed at the tip of the electrode rod 26 so that, when a high frequency current is passed through this tip electrode 26a, the tip electrode 26a may be used in such treatment as resecting or incising an affected part (such as a prostate) or stopping bleeding in a bleeding part.

As shown in FIG. 3, the electrode rod 26 inserted through the electrode guide tube 32 is kept water-tight by an O-ring 45 fitted in an inserting hole part at the rear end of the guide tube 32 within the connecting part 29.

An inserting hole 46 in which the electrode rod 26 can be inserted is made on the front surface of the slider in the position opposed to the rear end of the above mentioned electrode guide tube 32. Near the rear end of the electrode rod 26 inserted in this inserting hole 46, the insulating coating covering the electrode rod 26 is removed and the (electrode) conductor part 26b is exposed. A water-tight O-ring 47 is fitted in the inlet part of this inserting hole 46. This inserting hole 46 communicates in the depths with a recess 48 provided from the side (upper side in FIG. 1) and is widened. In the depths of the recess 48 communicating with the inserting hole 46, a guiding metal frame 52 fixing an electrode fixing member 51 is contained and secured. This metal frame 52 is provided in the position facing the above mentioned inserting hole 46 with a hole (or incision) 53 through which the conductor part 26b can be passed and is provided on the inner wall surface opposed to this hole 53 with a recess 54 containing the conductor part 26b at the rear end. Therefore, in case the conductor part 26b is inserted to collide at the rear end with this recess 54, the electrode rod 26 will be regulated in the movement in the direction vertical to the axial direction.

There is formed an electrode fixing mechanism 41 wherein, in case this electrode conductor part 26b is inserted to contact at the rear end with the inner wall of this recess 54, as shown in FIG. 1, a projecting sloped part 55 of the electrode fixing member 51 will be engaged with an incision 26c provided near the rear end of the electrode conductor part 26b so as to be able to fix the electrode rod 26. The above mentioned incision 26c is a deep sloped incision on the base end part side and the above mentioned sloped part 55 is a sloped projection fitting the above mentioned incision 26c.

The metal frame 52 provided inside with a square guide groove 57 (with which the electrode fixing member 51 is engaged on the tip side so as to be slidable) is contained in the recess 48 of the slider 36 and is pressed and fixed on the top end surface (upper end surface in FIG. 1) with the end surface of a metal frame fixing member 58 provided with a male screw to be screwed with the screw hole part of the recess of the slider 36.

This metal frame fixing member 58 is substantially cylindrically formed of an insulating member. The inner periphery on the upper side of this cylindrical form is incised to be steppedly expanded in the diameter and a coil spring 59 as a resilient member is contained in the air gap part of this expanded diameter. This coil spring 59 contacts at one end with the stepped surface of the metal frame fixing member 58 and at the other end with a spring fixing member 61 vertically movable in sliding contact with the expanded part of this metal frame fixing member 58. Therefore, the spring fixing member 61 is energized in the direction of projecting out of the recess 48 with respect to the metal frame fixing member 58 screwed and fixed to the slider 36. This spring fixing member 61 is substantially cylindrical, is provided at the top with a flange and is secured through a cement 63 or the like with a cylindrical position adjusting member 62 having an outside diameter fitting the small diameter part of the above mentioned metal frame fixing member 58. Therefore, this position adjusting member 62 is energized together with the spring fixing member 61 in the direction of projecting out of the recess 48 (in the upward direction in FIG. 1), is provided at the lower end with a flange 62a projecting radially outward and is prevented from moving upward from the position of the contact of this flange 62a with the lower end surface 58a of the metal frame fixing member 58.

The above mentioned position adjusting member 62 is provided with a male screw 81 on the inner periphery on the tip side. The fixing member 51 slidably fitting this position adjusting member 62 is provided with a male screw 82 on the outer periphery on the top side. This male screw 82 is screwed with the above mentioned female screw 81. Therefore, when the above mentioned spring fixing member 61 is rotated on the top side, the position adjusting member 62 secured to this spring fixing member 61 will be rotated together but, on the other hand, as the fixing member 51 screwed with the female screw 81 of this position adjusting member 62 is engaged on the lower end side with the square or the like guide groove 57 preventing the rotation, (by the variation of the amount of screwing with the above mentioned female screw 81,) the fixing member 51 will be moved in the vertical direction.

An incision 64 incised in the vertical direction so as to be larger than the width through which at least the electrode rod 26 can be passed is made in the part near the lower end of the above mentioned fixing member 51. The inner wall surface at the lower end of this incision 64 is formed to be a sloped part 55 projecting to be gradually larger toward the depth side of the inserted electrode rod 26. It is a feature of the first embodiment that the height position within the recess 48 of this sloped part 55 can be moved by the rotation of the above mentioned spring fixing member 61. By the rotation of this spring fixing member 61, the sloped part 55 is set near a correct position facing the inserting hole 46 or the hole 53 communicating with this hole 46, for example, as shown in FIG. 1.

By the way, the flange at the top of the spring fixing member 61 is fixed to a thick hollow disc or grip 65 made easy to rotate. The spring fixing member 61 is covered on the top side with a cap 66 molded of such insulating member as of rubber. The metal frame fixing member 58 is provided with a peripheral groove on the outer surface near the top and is fitted with a watertight O-ring in contact with the cap 66 on the outer periphery of this peripheral groove. By the way, the metal frame 52 has a lead wire wound and secured at one end 68a as by soldering on the outer periphery on the upper side and secured at the other end 68b to the base of a conductor part 42a of an electric cord connector 42 shown in FIG. 3 so as to electrically connect the metal frame 52 and fixing member 51 side fitted with the conductor part 26b of the electrode rod 26 with the electric cord connector 42 side.

According to the thus formed first embodiment, in case the electrode rod 26 is inserted on the rear end side through the inserting hole 46 and the hole 53 of the metal frame 52 communicating with this inserting hole 46 so as to be fitted to the electrode fixing mechanism part 41 of the slider 36, the electrode rod will be fitted on the tip side into the guide groove 57 of this metal frame 52. The incision 64 is provided in the part into which the electrode rod 26 is fitted. There is provided a mechanism of adjusting the height position of the electrode fixing member 51 in which the sloped part 55 to be engaged with the incision 26c near the rear end of the above mentioned electrode rod 26 is formed on one surface of this incision 64.

Therefore, even in case the respective parts forming this electrode fixing mechanism fluctuate, if the cap 66 is removed and the spring fixing member 61 is rotated at the top, the electrode fixing member 51 screwed to the position adjusting member 62 secured to this spring fixing member 61 will slide in the guide groove 57 within the above mentioned metal frame 52 and the height position of the sloped part 55 will be able to be adjusted. By this adjustment, for example, if the sloped part 55 can be seen through the electrode inserting hole 46, it will be set in a proper position. Then, if the cap 66 is applied and the electrode rod 26 is inserted into the inserting hole 46, the electrode rod 26 will contact at the rear end with the sloped part 55 and, if the electrode rod 26 is further pressed from this state to move this sloped part 55 energized by the coil spring 59 and is inserted to the depth side to ride over this sloped part 55, when this electrode rod 26 nearly collides at the rear end with the recess 54 of the metal frame 52, the sloped part 55 will be engaged with the incision 26c of the electrode rod 26 and the electrode rod 26 will be positively automatically fixed without any backlash.

On the other hand, in releasing this electrode rod 26, when the cap 55 is pressed inward of the recess 48 against the energizing force of the coil spring 59 to move the electrode fixing member 51, the sloped part 55 and the incision 26c of the electrode rod 26 will be able to be disengaged with each other and, in this state, the electrode rod 26 will be able to be pulled out.

Figure 4:
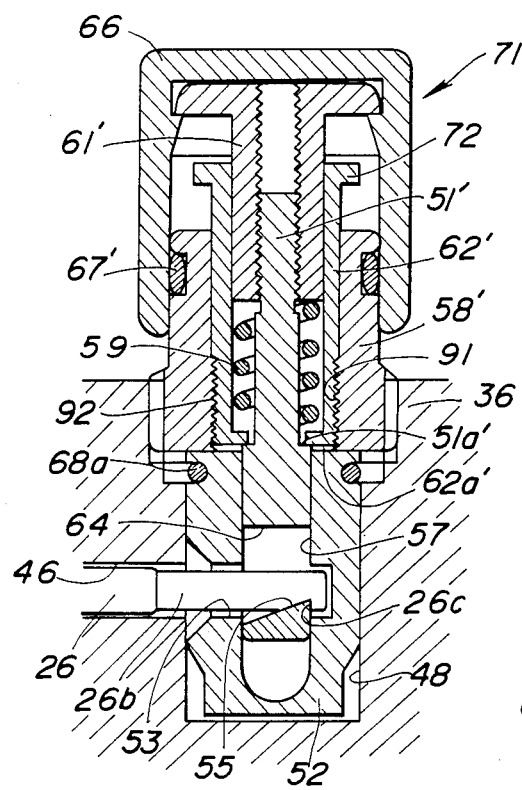
FIGS. 4 and 5 relate to the second embodiment of the present invention.

FIG. 4 shows the second embodiment of the present invention.

In an electrode fixing mechanism part 71 of this second embodiment, a female screw 91 is formed on the inner periphery at the lower end of a metal frame fixing member 58' and a male screw 92 of a position adjusting member 62' having a flange 72 provided to project at the top is screwed in the above mentioned female screw 91 so that, when this flange 72 is rotated, the position adjusting member 62' will be moved in the vertical direction (in FIG. 4) with respect to the metal frame fixing member 58' screwed to the slider 36. This position adjusting member 62' is provided with a projection 62a' on the inner periphery at the lower end, is internally fitted with the coil spring 59 contacting at the lower end with this projection 62a' and is further internally fitted above this coil spring 59 with a spring fixing member 61' with which this coil spring 59 contacts at the upper end. A screw hole is formed on the inner periphery of the spring fixing member 61' energized upward by this coil spring 59 and an electrode fixing member 51' having a male screw formed on the upper side is screwed in the above mentioned screw hole. The electrode fixing member 51' screwed with this spring fixing member 61' is energized upward together with the spring fixing member 61' by the above mentioned coil spring 59 and a wide steped part 51a' fitted in the guide groove 57 is prevented from moving upward from the position of contacting the projection 62a' at the lower end of the position adjusting member 62'.

The others are substantially of the same formation as in the first embodiment. The same reference numerals are attached to the same members.

Figure 5:
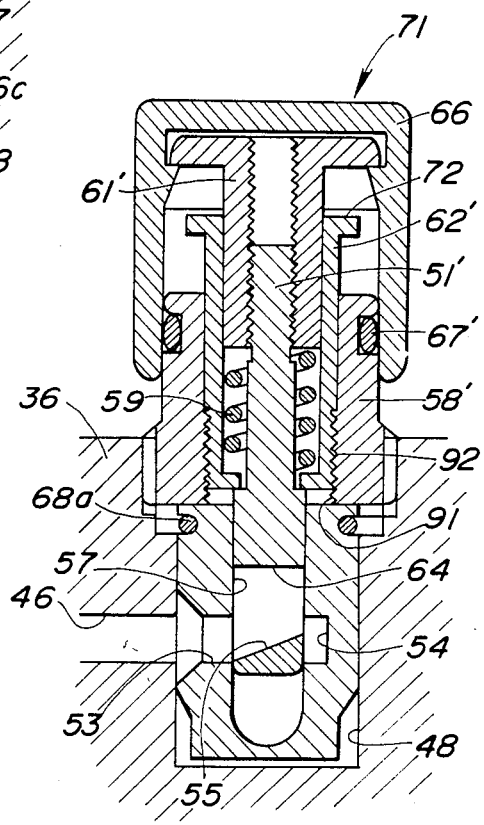
Figure 6:
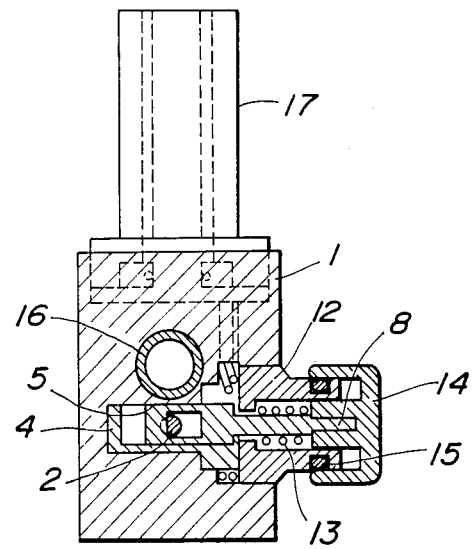
FIGS. 6 and 7 relate to a related art example.
Figure 7:
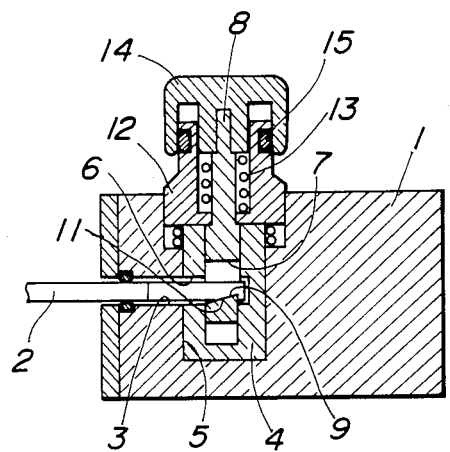

According to the thus formed second embodiment, when the cap 66 is removed and the flange 72 of the position adjusting member 62' is rotated, this position adjusting member 62' will vertically move with respect to the metal frame 52 and metal frame fixing member 58'. When this position adjusting member 62' moves vertically, the spring fixing member 61' slidably fitted above the coil spring 59 in the above mentioned metal frame fixing member 58' and energized upward by the energizing force of the coil spring 59 contacting at the lower with the projection 62a' at the lower end of this position adjusting member 62' will also vertically move and the electrode fixing member 51' screwed to this spring fixing member 61' will also vertically move. That is to say, when the above mentioned position adjusting member 62' is rotated to move vertically, the spring fixing member 61' and electrode fixing member 51' will move vertically to the metal frame 52 or metal frame fixing member 58' while keeping the same relation with the postion adjusting member 62' as before it is rotated. In FIG. 4, in case the position adjusting member 62' is rotated in one direction to be moved upward before the electrode rod 26 is inserted, it will be as in FIG. 5.

By the way, the electrode fixing member 51' and spring fixing member 61' may be secured to each other with a cement. In cases the energizing force of the coil spring 59 fluctuates in screwing, the screwing amount may be varied and adjusted to make a proper energizing force act.

By the way, the incision on the electrode rod 26 side may be in the form of a peripheral groove.

In the above mentioned respective embodiments, in case the electrode rod 26 to be inserted is not columnar on the rear end side but is in a form partly incised in the axial direction, it may be inserted only when the position of the loop is in a proper direction.

As described above, according to the present invention, in an electrode fixing mechanism removably fitting an electrode, as a means of adjusting the position of a sloped locking part engaging with a recess formed in the electrode near the rear end is provided, even in case the parts forming the electrode fixing mechanism fluctuate, a proper position can be simply set and the electrode can be positively fixed.

In this invention, it is apparent that working modes different in a wide range can be formed on the basis of this invention without deviating from the spirit and scope of the invention. This invention is not restricted by its specific working mode except being limited by the appended claims.

What is claimed is:

1. A resectoscope comprising:
    a hollow sheath;
    an observing scope inserted in said sheath;
    a resecting electrode means inserted through said sheath;
    a handle part having a slider connected to said sheath, having said electrode means connected at the base end to it and moving said electrode means forward and rearward in the axial direction; and
    an electrode fixing mechanism having:
    an inserting hole which is provided in said slider and in which said electrode means is inserted at the base end;
    an engaging part provided in the base end part of said electrode means inserted in said inserting hole;
    an electrode fixing member having a locking part engaged with said engaging part provided in said electrode means to lock said electrode means and movable in the direction intersecting with the axis of said electrode means;
    an energizing means energizing said electrode fixing member in the direction of fixing said electrode means;
    an electrode fixing mechanism fixing means fixing said electrode fixing member and said energizing means to said slider; and
    a position adjusting means making the position of said electrode fixing member with respect to said slider adjustable in the diretion intersecting with the axis of said electrode means.

2. A resectoscope according to claim 1 wherein said position adjusting means is interposed between said electrode fixing member and said electrode fixing mechanism fixing means.

3. A resectoscope according to claim 2 wherein said position adjusting means has said electrode fixing member fitted movably in the direction intersecting with the axis of said electrode means and has a position adjusting member restricted in the movement in the energizing direction by said energizing means.

4. A resectoscope according to claim 3 wherein said electrode fixing member is movably screwed to said position adjusting member.

5. A resectoscope according to claim 4 wherein a metal frame having a guide groove guiding said electrode fixing means is provided within said inserting hole and said electrode fixing member is contained in said guide groove and has a sliding part prevented from rotating with respect to said guide groove and slidable in the direction intersecting with the axis of said electrode means.

6. A resectoscope according to claim 4 wherein a metal frame fixing member fixing said metal frame to said slider is provided, said position adjusting member is movably contained within said metal frame fixing member and said energizing means is interposed between said metal frame fixing member and said position adjusting member.

7. A resectoscope according to claim 6 wherein said energizing means is formed of a resilient material locked at one end to said metal frame fixing member and at the other end to a resilient material fixing member fixed to said position sdjusting member.

8. A resectoscope according to claim 2 wherein said position adjusting means restricts the movement in the energizing direction of said electrode fixing member and has a position adjusting member movable in the direction intersecting with the axis of said electrode means with respect to said electrode fixing mechanism fixing means.

9. A resectoscope according to claim 8 wherein a metal frame having a guide groove guiding said electrode fixing means is provided within said inserting hole, said electrode fixing member is contained in said guide groove and has a sliding part prevented from rotating with respect to said guide groove and slidable in the direction intersecting with the axis of said electrode means.

10. A resectoscope according to claim 9 wherein a metal frame fixing member fixing said metal frame to said slider is provided, said position adjusting member is movably screwed to said metal frame fixing member and said energizing means is interposed between said electrode fixing member and said position adjusting member.

11. A resectoscope according to claim 10 wherein said energizing means is formed of a resilient material locked at one end to said position adjusting member and at the other end to a resilient material fixing member fixed to said electrode fixing member.

12. A resectoscope according to claim 1 wherein said engaging part is a deep inclined incision on the base end side and said locking part is an inclined projection fitting said incision.

* * * * *